(12) United States Patent
Charles et al.

(10) Patent No.: US 12,226,155 B2
(45) Date of Patent: Feb. 18, 2025

(54) IMAGING MARKERS FOR VERIFYING BIOMETRY

(71) Applicant: Alcon Inc., Fribourg (CH)

(72) Inventors: Steven T. Charles, Memphis, TN (US); Sahar Hosseinzadeh Kassani, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 651 days.

(21) Appl. No.: 17/477,682

(22) Filed: Sep. 17, 2021

(65) Prior Publication Data
US 2022/0095909 A1 Mar. 31, 2022

Related U.S. Application Data

(60) Provisional application No. 63/083,566, filed on Sep. 25, 2020.

(51) Int. Cl.
| | | |
|---|---|---|
| *A61B 3/14* | (2006.01) | |
| *A61B 3/00* | (2006.01) | |
| *A61B 3/10* | (2006.01) | |
| *A61B 3/12* | (2006.01) | |
| *G06T 7/00* | (2017.01) | |
| *G06T 7/11* | (2017.01) | |

(52) U.S. Cl.
CPC .......... *A61B 3/0058* (2013.01); *A61B 3/1005* (2013.01); *A61B 3/102* (2013.01); *A61B 3/12* (2013.01); *G06T 7/0012* (2013.01); *G06T 7/11* (2017.01); *G06T 2207/10101* (2013.01); *G06T 2207/30041* (2013.01)

(58) Field of Classification Search
CPC ..... A61B 3/0058; A61B 3/1005; A61B 3/102; A61B 3/12; G06T 7/0012; G06T 7/11; G06T 2207/10101; G06T 2207/30041
USPC .................................................. 351/206, 246
See application file for complete search history.

(56) References Cited

U.S. PATENT DOCUMENTS

| | | |
|---|---|---|
| 2013/0235343 A1 | 9/2013 | Hee et al. |
| 2015/0250384 A1 | 9/2015 | Volkwardt et al. |
| 2016/0284103 A1* | 9/2016 | Huang ...................... G06T 7/30 |
| 2021/0209758 A1* | 7/2021 | Buckland .............. G06F 18/243 |

* cited by examiner

*Primary Examiner* — Mahidere S Sahle

(57) ABSTRACT

The systems and methods described herein provide improved techniques for displaying imaging markers for verifying biometry. A method includes receiving an indication to initiate a first optical coherence tomography (OCT) scanning of an eye; initiating, based on the received indication, the first OCT scanning of the eye; generating, based on the first OCT scanning, a first OCT image of the eye; detecting, based on the first OCT image, a retinal pigment epithelium (RPE) and a fovea in the eye; based on the detecting, causing a first enhanced OCT image to be displayed to a user, the first enhanced OCT image displaying: a first virtual marker segmenting at least a portion of the detected RPE, and a second virtual marker, where the second virtual marker visually identifies a location of the detected fovea, and where the second virtual marker is a radial line through the location of the detected fovea.

13 Claims, 5 Drawing Sheets

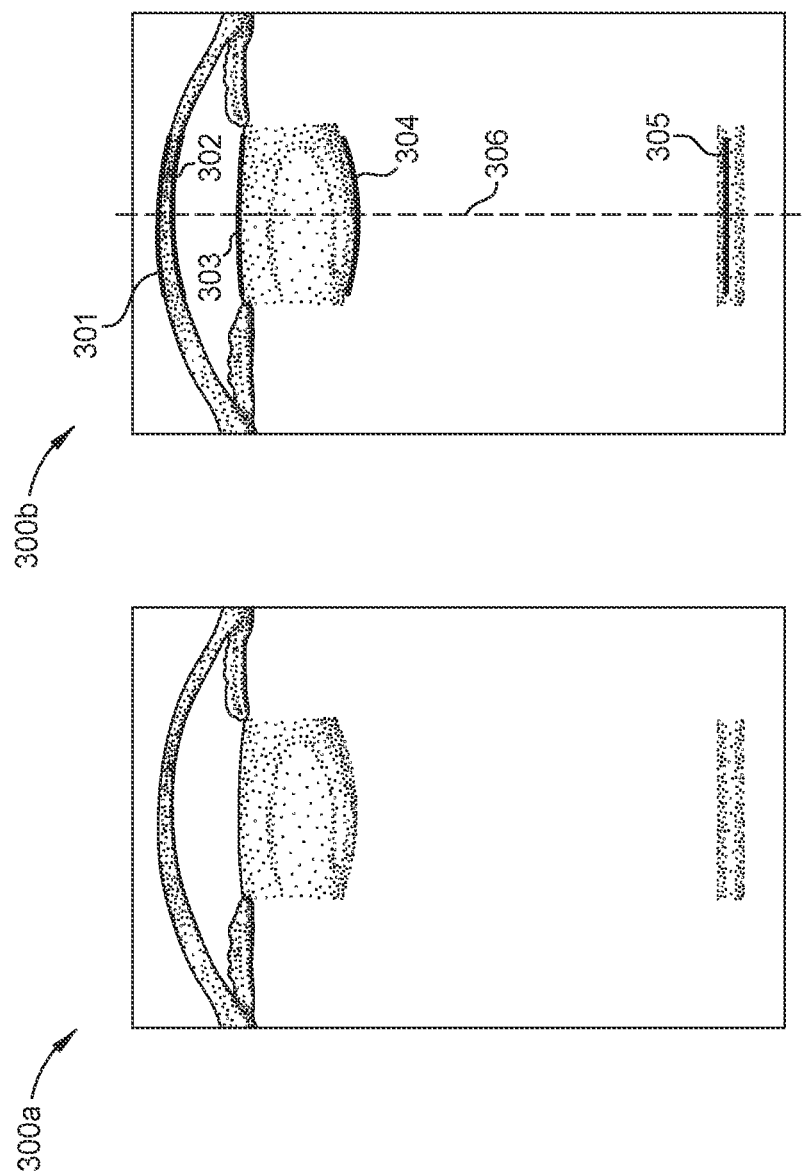

IMAGING MARKERS FOR VERIFYING BIOMETRY

BACKGROUND

Field

Embodiments of the present disclosure generally relate to methods and apparatus for ophthalmic imaging, and more particularly, to methods and apparatus for displaying imaging markers on ophthalmic images for verifying biometry provided by a biometry system.

Description of the Related Art

Anatomical characteristics and dimensions of an eye of a patient may be measured prior to performing ophthalmic surgeries, such as cataract surgeries. Certain interrelationships between the structures of the eye and the measured dimensions affect determination and selection of the correct lens power for the patients that undergo ophthalmic surgeries. One such measurement and interrelationship between the components of the eye is the axial length of the eye.

The axial length of the eye is generally measured during an optical biometry of the patient. The axial length is the distance between the anterior surface of the cornea of the eye and the RPE in the fovea of the eye. However, various macular abnormalities and/or diseases, such as macular holes, age-related macular degeneration, vitreomacular traction syndrome, vitreomacular schisis, epimacular membrane, and the like, may cause anatomical changes in the eye. Such anatomical changes in the eye may affect the measurement of the axial length by existing systems. For example, when measuring the axial length of an eye with a macular hole, certain existing biometry systems may measure the length from the elevated tissue around the macular hole instead of the RPE in the fovea.

Furthermore, existing biometry systems may not be capable of accurately detecting a macular abnormality in a patient's eye, and may consequently fail to alert a clinician and/or surgeon of the macular abnormality. Failing to alert the user of the macular abnormality may cause the user to implant an incorrect lens with an incorrect lens power in the patient, which may cause the patient to undergo additional surgeries to correct the implantation of the incorrect lens.

SUMMARY

The present disclosure generally relates to methods and apparatus for displaying imaging markers on ophthalmic images for verifying biometry.

In certain embodiments, a method generally includes receiving an indication to initiate a first optical coherence tomography (OCT) scanning of an eye. The method further includes initiating, based on the received indication, the first OCT scanning of the eye. The method also includes generating, based on the first OCT scanning, a first OCT image of the eye. The method further includes detecting, based on the first OCT image, a retinal pigment epithelium (RPE) of the eye and a fovea in the eye. The method also includes, based on the detecting, causing a first enhanced OCT image to be displayed to a user, the first enhanced OCT image displaying: a first virtual marker segmenting at least a portion of the detected RPE, where the first virtual marker is a curvilinear line, and a second virtual marker, where the second virtual marker visually identifies a location of the detected fovea, and where the second virtual marker is a radial line.

Aspects of the present disclosure provide means for, apparatus, processors, and computer-readable mediums for performing the methods described herein.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3A illustrates an example OCT image of an eye, in accordance with an illustrative implementation of the present disclosure.

FIG. 3B illustrates an example enhanced OCT image of an eye, in accordance with an illustrative implementation of the present disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to methods and apparatus for displaying imaging markers on ophthalmic images for verifying biometry.

Axial length measurements are critical in selecting the correct intraocular lens with the correct lens power for a patient. Macular abnormalities and/or diseases may affect axial length measurements performed by existing systems. For example, a macular hole may cause an existing system to select an incorrect location away from the fovea as the location of the fovea. Similarly, macular abnormalities may affect the existing systems' ability to measure from a correct depth of the eye. For example, when macular abnormalities, such as an elevated macula, are present in an eye, an existing system's axial length measurement from a macular surface of the elevated macula may result in a shorter axial length measurement. The existing systems fail to provide any visual indication to a user (e.g., clinician, surgeon, and the like) of how the axial length of the patient is measured. Failing to provide visual indication of how the axial length of the patient is measured fails to provide the user an efficient and an easy way to verify the axial length measurements by the system.

Accordingly, some implementations of the present disclosure provide various systems and techniques that improve a user's ability to efficiently verify whether axial length measurements are accurate and performed correctly by an imaging system. In some implementations, the techniques for improving a user's ability to efficiently verify the accuracy of the axial length measurements are based on visual indicators provided on an image displayed to the user.

Figure 1:
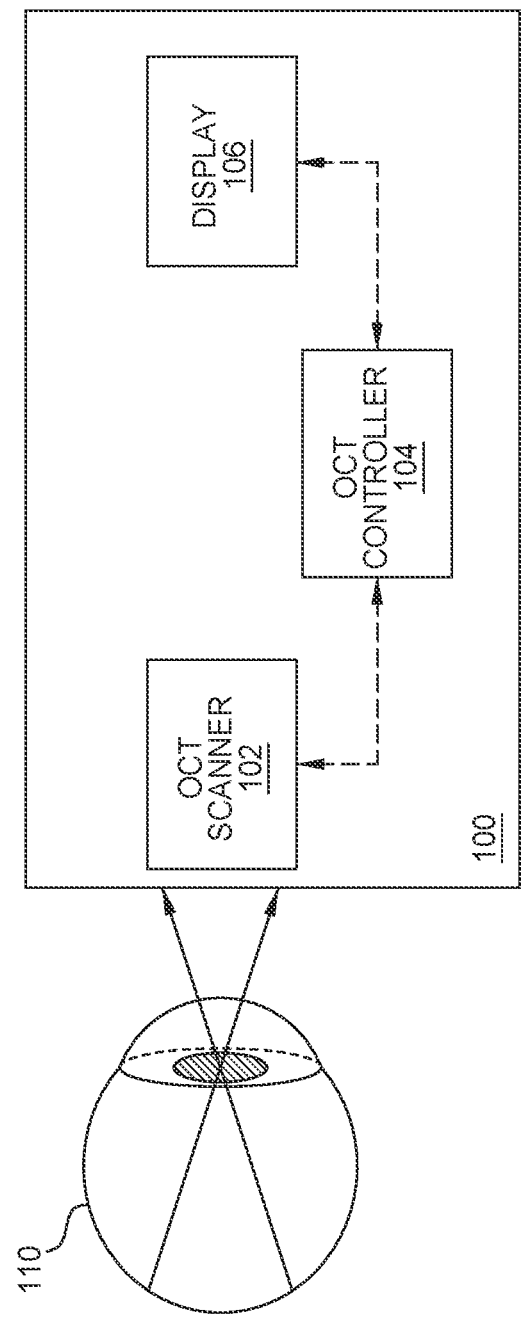
FIG. 1 illustrates a block diagram of selected components of an example imaging system, in accordance with an illustrative implementation of the present disclosure.

FIG. 1 illustrates a block diagram of selected components of an example imaging system 100. The imaging system 100 includes an optical coherence tomography (OCT) scanner 102, an OCT controller 104, and a display 106.

The OCT scanner 102 may include a number of OCT components and/or instruments (not shown separately). The OCT components and/or instruments may be of various types, and the OCT scanner 102 may be configured differently based on the types of the OCT components and/or instruments. In some implementations, the OCT scanner 102 may be configured as a time domain OCT (TD-OCT). In some implementations, the OCT scanner 102 may be configured as a frequency domain OCT (FD-OCT). In some implementations, the OCT scanner 102 may be configured as a swept-source OCT (SS-OCT).

The OCT scanner 102 performs OCT scanning of an eye 110 of a patient. The OCT scanner 102 may perform the OCT scanning by controlling output of one or more sample beams (not shown) onto the eye 110, and receiving one or more measurement beams (not shown) reflected back from the eye 110. The one or more measurement beams may be reflected back from the eye 110 in response to the photons of the sample beam interacting with the tissue in the eye 110. The OCT scanner 102 may be configured to move the sample beam to a certain location of the eye in response to receiving a command and/or location information from the OCT controller 104.

The OCT scanner 102 may be configured to scan the eye 110 at various depths of the eye 110. For example, the OCT scanner 102 may be configured to scan the entire depth of the eye 110 for a full eye scan of the eye 110. Similarly, the OCT scanner 102 may be configured to scan any portion of the eye 110, such as the retina of the eye 110. In some implementations, the OCT scanner 102 may scan different depths of the eye 110 at different resolutions. For example, the OCT scanner 102 may scan the entire depth of the eye 110 at a lower resolution, and may scan a portion of the eye 110, such as the retina of the eye 110, at a higher resolution.

The OCT scanner 102 may be configured to generate scan data based on the one or more measurement beams reflected back from the eye. The scan data may represent a depth profile of the scanned tissue. In some implementations, the scan data generated by the OCT scanner 102 may include two-dimensional (2D) scan data of a line scan (B-scan). In some implementations, the scan data generated by the OCT scanner 102 may include three-dimensional (3D) scan data of an area scan (C-scan, en face). The OCT scanner 102 may be configured to transmit the generated scan data to the OCT controller 104. In some implementations, the OCT scanner 102 may be configured to transmit the generated scan data in real-time or near real-time. In some implementations, the OCT scanner 102 may be configured to transmit the generated scan data after the entire scanning operation is completed by the OCT scanner 102.

The OCT scanner 102 may be configured to initiate scanning of the eye 110 in response to receiving a command and/or instruction from the OCT controller 104. The OCT controller 104 may be configured to transmit a scan initiation command to the OCT scanner 102 in response to receiving an indication from a user, such as a surgeon, clinician, medical personnel, and the like, to initiate scanning of the eye. In some implementations, the indication from the user may provide information related to depth and/or location of the eye for scanning, and the OCT controller 104 may be configured to provide the received eye depth and/or location related information to the OCT scanner 102. For example, an indication received by the OCT controller 104 may indicate a full eye OCT scan, and the OCT controller 104 may transmit an instruction to the OCT scanner 102 that indicates a full eye OCT scan. Similarly, an indication received by the OCT controller 104 may indicate an OCT scan of the retina of the eye, and the OCT controller 104 may transmit an instruction to the OCT scanner 102 that indicates an OCT scan of the retina of the eye.

The OCT controller 104 may be configured to receive the indication to initiate scanning of the eye via a user interface (e.g., a graphical user interface (GUI)) and/or an input device (not shown). Input devices may be communicatively coupled to and/or incorporated with the imaging system 100. Examples of input devices include, but are not limited to, a key pad, a keyboard, a touch screen device configured to receive touch inputs, and the like.

The OCT controller 104 may be communicatively coupled to the OCT scanner 102 via one or more electrical and/or communication interfaces. In some implementations, the one or more electrical and/or communication interfaces may be configured to transmit data (e.g., scan data generated by the OCT scanner 102) from the OCT scanner 102 at a high transmission rate such that the OCT controller 104 may receive the data in real-time or near real-time from the OCT scanner 102.

The OCT controller 104 may be configured to generate one or more OCT images based on the received generated scan data from the OCT scanner 102. For example, the OCT controller 104 may be configured to generate a 2D image or a B-scan image based on the generated 2D scan data of a line scan. Similarly, the OCT controller 104 may be configured to generate a 3D image or a C-scan based on the generated 3D scan data of an area scan. The OCT controller 104 may be configured to perform image generation and/or image processing in real-time and/or near real-time.)

The OCT controller 104 may be configured with one or more tissue detection and/or auto-segmentation algorithms to detect and/or auto-segment one or more tissue layers of the eye in the generated OCT images. Examples of tissue layers of an eye that the OCT controller 104 may be configured to detect and/or auto-segment include, but are not limited to, fovea, retinal pigment epithelium (RPE), anterior surface of the cornea, retina, cornea, iris, pupil, anterior and posterior surface plus the position of the lens, and the like. The OCT controller 104 may be configured to apply one or more tissue detection and/or auto-segmentation algorithms on the received scan data from the OCT scanner 102 and/or the generated OCT images to detect and/or auto-segment one or more tissue layers of the scanned eye.

Based on the received scan data from the OCT scanner 102 and/or the generated OCT images, the OCT controller 104 may be configured to generate enhanced OCT images by generating and/or displaying one or more virtual markers on one or more OCT images to visually identify one or more detected and/or auto-segmented tissue layers of the eye.

The OCT controller 104 may be configured to generate and/or display one or more virtual markers on an OCT image (e.g., the generated OCT image) to visually identify one or more detected and/or auto-segmented tissue layers of the eye. For example, the OCT controller 104 may be configured to detect and/or auto-segment the fovea of the eye on an OCT image, and generate and/or display a virtual marker on the OCT image to visually identify a location of the fovea and/or segment at least a portion of the fovea. Similarly, the OCT controller 104 may be configured to detect and/or auto-segment RPE of the eye on an OCT image, and generate and/or display a virtual marker on the OCT image to visually identify a location of the RPE and/or segment at least a portion of the RPE.

The OCT controller 104 may be configured to generate and/or display the virtual markers in various shapes and/or sizes. For example, the OCT controller 104 may be configured to generate and/or display virtual markers that are curved, such as curvilinear lines. Similarly, the OCT controller 104 may be configured to generate and/or display virtual markers that are straight lines and/or radial lines that converge to and/or through a location in the eye (e.g., a location of a detected fovea in the eye). The OCT controller 104 may be configured to generate enhanced OCT images by generating and/or displaying virtual markers on OCT images (e.g., the OCT images generated by the OCT controller 104).

In some implementations, based on the OCT images and/or scan data, the OCT controller 104 may be configured to detect an abnormal macular anatomic configuration (e.g., abnormal macular condition) in the eye 110. In response to detecting the abnormal macular anatomic configuration, the OCT controller 104 may be configured to transmit an alert to the user advising against using a contrast decreasing multi-focal intraocular optical lens (IOL) or extended depth of focus (EDOF) IOL. In some implementations, the OCT controller 104 may be configured to periodically transmit the alert until the OCT controller 104 receives a confirmation from a user acknowledging the alert.

The OCT controller 104 may be configured to cause OCT images and/or the enhanced OCT images to be displayed to a user by providing the images to the display 106 to be displayed to the user. The OCT controller 104 may be communicatively coupled and/or electrically connected to the display 106. The display 106 may be configured in compliance with one or more display standards and may be of any various types of displays, such as video graphics array (VGA), extended graphics array (XGA), digital visual interface (DVI), high-definition multimedia interface (HDMI), and the like.

Figure 2:
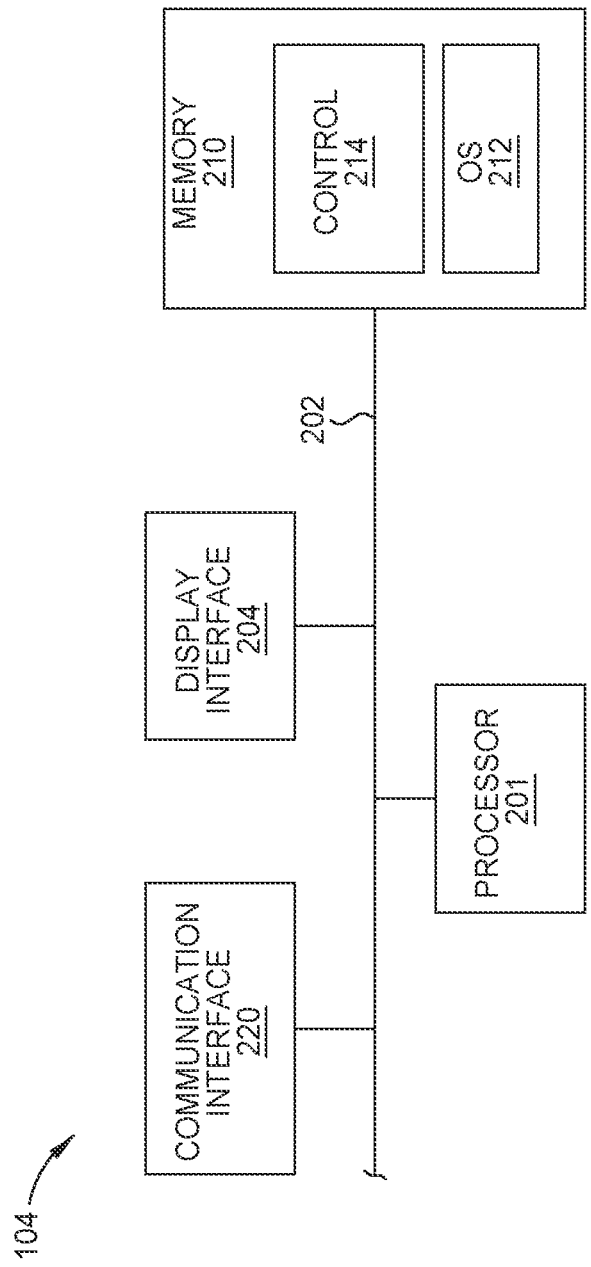
FIG. 2 illustrates a block diagram of selected components of an OCT controller, in accordance with an illustrative implementation of the present disclosure.

FIG. 2 illustrates a block diagram of selected components of an implementation of an OCT controller, such as the OCT controller 104 as described above in reference with FIG. 1. As shown in FIG. 2, OCT controller 104 includes processor 201, bus 202, display interface 204, memory 210, communication interface 220.

The processor 201 may be communicatively coupled to memory 210, display interface 204, and communication interface 220 via bus 202. The OCT controller 104 may be configured to interface with various external components (e.g., OCT scanner 102, display 106) of an imaging system (e.g., imaging system 100) via processor 201 and communication interface 220. In some implementations, communication interface 220 may be configured to enable OCT controller 104 to connect to a network (not shown). In some implementations, the OCT controller 104 may be connected to one or more displays, such as display 106, via display interface 204.

The memory 210 may include persistent, volatile, fixed, removable, magnetic, and/or semiconductor media. The memory 210 may be configured to store one or more machine-readable commands, instructions, data, and/or the like. In some implementations, as shown in FIG. 2, the memory 210 may include one or more sets and/or sequences of instructions, such as an operating system 212, a scanning control application 214, and the like. Examples of operating system 212 may include, but are not limited to, UNIX or UNIX-like operating system, a Windows® family operating system, or another suitable operating system. The scanning control application 214 may be configured to perform OCT controller operations as described herein including, but not limited to, operations related to initiation of scanning of the eye, generation of OCT images, OCT image processing, generation and/or displaying of virtual markers on OCT images, generation of enhanced OCT images, and the like.

FIG. 3A illustrates an example OCT image 300a of an eye (e.g., the eye 110). The OCT image 300a, as shown in FIG. 3A, is a full eye OCT scan. As described above, the OCT controller 104 may be configured to generate the OCT image 300a based on the scan data received from the OCT scanner 102. As described above, the OCT controller 104 may be configured to detect and/or auto-segment one or more tissue layers of the eye based on the generated OCT images and/or the received scan data. Further, the OCT controller 104 may be configured to generate and/or display, in an enhanced OCT image, virtual markers visually indicating one or more of the detected and/or auto-segmented tissue layers.

FIG. 3B illustrates an example enhanced OCT image 300b of the eye (e.g., the eye 110) generated based on the OCT image 300a. As shown in the example of FIG. 3B, the OCT controller 104 detects an anterior surface and posterior portion of the cornea of the eye and generates and/or displays virtual markers 301 and 302 that visually identify the anterior surface and posterior portion of the cornea of the eye, respectively. In the example of FIG. 3B, the OCT controller 104 detects the pupil of the eye and generates and/or displays a virtual marker 303 that visually identifies a location and/or at least a portion of the pupil in the enhanced OCT image 300b. Similarly, the OCT controller 104 detects a lens and/or a posterior portion of the lens of the eye, and generates and/or displays a virtual marker 304 that visually identifies an anterior and/or posterior portion of the lens of the eye in the enhanced OCT image 300b. The OCT controller 104 may detect and/or auto-segment a fovea and the RPE of the eye, and generate and/or display virtual markers 305 and 306 that visually identify locations of the RPE and the fovea, respectively, in the enhanced OCT image 300b. As shown in FIG. 3B, the virtual marker 306 intersects a middle portion of the detected and/or auto-segmented portion of the fovea.

As described above, the OCT controller 104 may be configured to generate and/or display virtual markers that may be of various shapes and sizes. For example, as shown in FIG. 3B, the shape of the virtual markers 301 and 302 are curved, while the shape of the virtual marker 306 is straight. In some implementations, the virtual marker 306 may be a radial line that converges to a location of the detected fovea. In some implementations, the shapes and/or sizes of the virtual makers may reflect and/or match the shapes and/or sizes of the tissue layers displayed OCT images. For example, the curvature of the virtual marker 301 matches curvature of the anterior surface of the cornea of the eye, and the curvature of the virtual marker 302 matches curvature of the posterior portion of the cornea of the eye. Similarly, the virtual marker 305 may be a curvilinear line and the curvilinear line matches a posterior curvature of the eye 110.

The OCT controller 104 may be configured to generate and/or display one or more virtual markers that visually identify portions of the eye upon which biometric measurements are performed by the OCT controller 104. For example, as described above, an axial length of the eye is the distance between the fovea of the eye and an anterior surface of the eye. Therefore, in some implementations, the OCT controller 104 may be configured to generate and/or display the virtual marker 306 in a manner such that the virtual marker 306 may extend at least from the anterior surface of the cornea of the eye and through the fovea of the eye. In some implementations, the OCT controller 104 may be configured to generate and/or display the virtual marker 306 in a manner such that the virtual marker 306 may extend from a portion anterior to the retina and through the fovea of the eye.

As described above, abnormal macula conditions and/or macular diseases may cause anatomical changes of the macula, and certain existing OCT imaging system may fail to detect the abnormal macula condition and/or disease, resulting in an incorrect axial length measurement without providing any mechanism to the user to verify that the measurement is correct and/or providing any alert to user of the macular condition and/or disease. The OCT controller 104, however, by generating and/or displaying the virtual markers, visually indicates the tissue layers detected by the imaging system 100 (e.g., via the OCT controller 104) to the user, and allows the user to determine whether the biometric measurements are made from the correct locations and sufficient depths of the eye.

For example, in FIG. 3B, the OCT controller 104 generates and/or displays a virtual marker 305 along the detected and/or auto-segmented RPE of the eye, and generates and/or displays the virtual marker 306 that intersects the virtual marker 305 to visually indicate to the user that the axial length measurement is being made from a correct portion of the eye, e.g., the fovea of the eye, and not from an incorrect portion of the eye, e.g., a macular hole of the eye. Thus, the virtual markers generated and/or displayed by the OCT controller 104 on the enhanced OCT images, as described herein, allow the user to efficiently confirm that the imaging system 100 correctly measured the axial length measurements.

As described above, in some implementations, the OCT controller 104 may be configured to initiate scans at various depths of the eye and/or at different resolutions to provide the user with additional OCT enhanced images that also allow the user to verify whether the biometric measurements (e.g., axial length) are accurate. For example, in response to the completion of the OCT scanning for image 300a of FIG. 3A, the OCT controller 104 may initiate a scan of the retina of the eye.

Figure 4B:
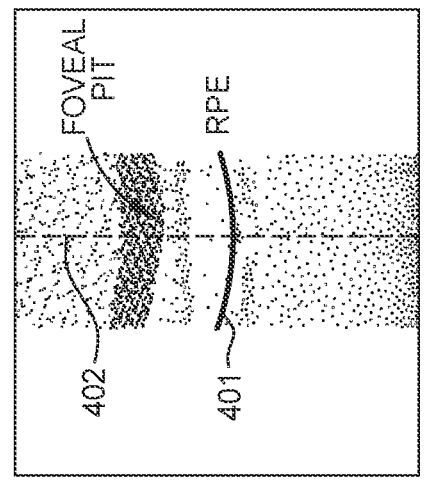
FIG. 4B illustrates an example enhanced OCT image of a retina of an eye, in accordance with an illustrative implementation of the present disclosure.
Figure 4A:
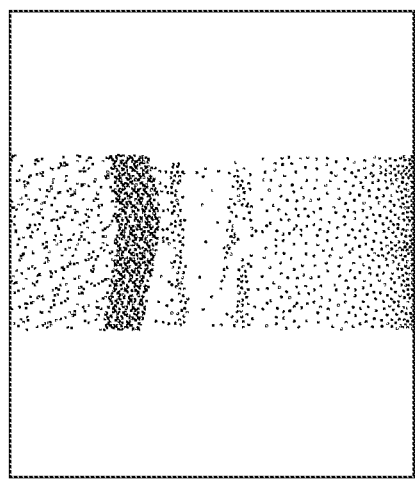
FIG. 4A illustrates an example OCT image of a retina of an eye, in accordance with an illustrative implementation of the present disclosure.

FIG. 4A illustrates an example OCT image 400a of a retina of an eye (e.g., eye 110). The OCT controller 104 may generate the OCT image 400a based on the scan data of the retina received from the OCT scanner 102. The OCT controller 104 may be configured to detect and/or auto-segment tissue layers of the retina, such as the fovea, the RPE, and the like, based on the scan data of the retina and/or the OCT image 400a of the retina. The OCT controller 104 may be configured to generate and/or display virtual markers on an enhanced OCT image, such as the example enhanced OCT image 400b of FIG. 4B, to visually identify the detected and/or auto-segmented tissue layers of the retina.

The enhanced OCT image 400b of FIG. 4B is an example enhanced OCT image generated based on OCT image 400a. In the example enhanced OCT image 400b, the OCT controller 104 generates and/or displays virtual markers 401, and 402, to visually identify the detected and/or auto-segmented RPE, and foveal pit of the eye, respectively. The virtual marker 401 may be a curvilinear line. The curvature of the curvilinear line of virtual marker 401 may match a posterior curvature of the eye 110. The virtual marker 402 may be a radial line that converges to a location of the detected fovea. The OCT controller 104 may be configured to generate and/or display one or more virtual markers on an enhanced OCT image of a shallower depth that correspond to one or more virtual markers generated and/or displayed on a previous enhanced OCT image of a deeper depth for the same patient. For example, in image 400b, as shown in FIG. 4B, the virtual marker 402, which visually identifies a location and/or segments at least a portion of the foveal pit, corresponds to the virtual marker 306 of FIG. 3B that visually identifies the location and/or segments at least the portion of the foveal pit in the enhanced OCT image 300b. Similarly, virtual marker 401, which visually identifies and/or segments at least a portion of the RPE, corresponds to the virtual marker 305 of FIG. 3B that visually identifies the location and/or segments at least the portion of the RPE in the enhanced OCT image 300b.

Therefore, by generating and/or displaying corresponding virtual markers on enhanced OCT images of different depths, the OCT controller 104 allows a user to verify the accuracy of the biometric measurements and/or the accuracy of measurement locations within the eye of the patient in more detail. For example, the OCT controller 104 may generate and/or display a radial virtual marker (e.g., virtual marker 306 and virtual marker 402) through the fovea and a curvilinear virtual marker (e.g., virtual marker 306 and virtual marker 402) at the RPE on an OCT scan (e.g., enhanced OCT images 300b and 400b). The OCT controller 104 may generate and/or display the radial virtual marker through the fovea at a location that perpendicularly intersects the curvilinear virtual marker at the RPE and/or segmenting a portion of the RPE.

Figure 5:
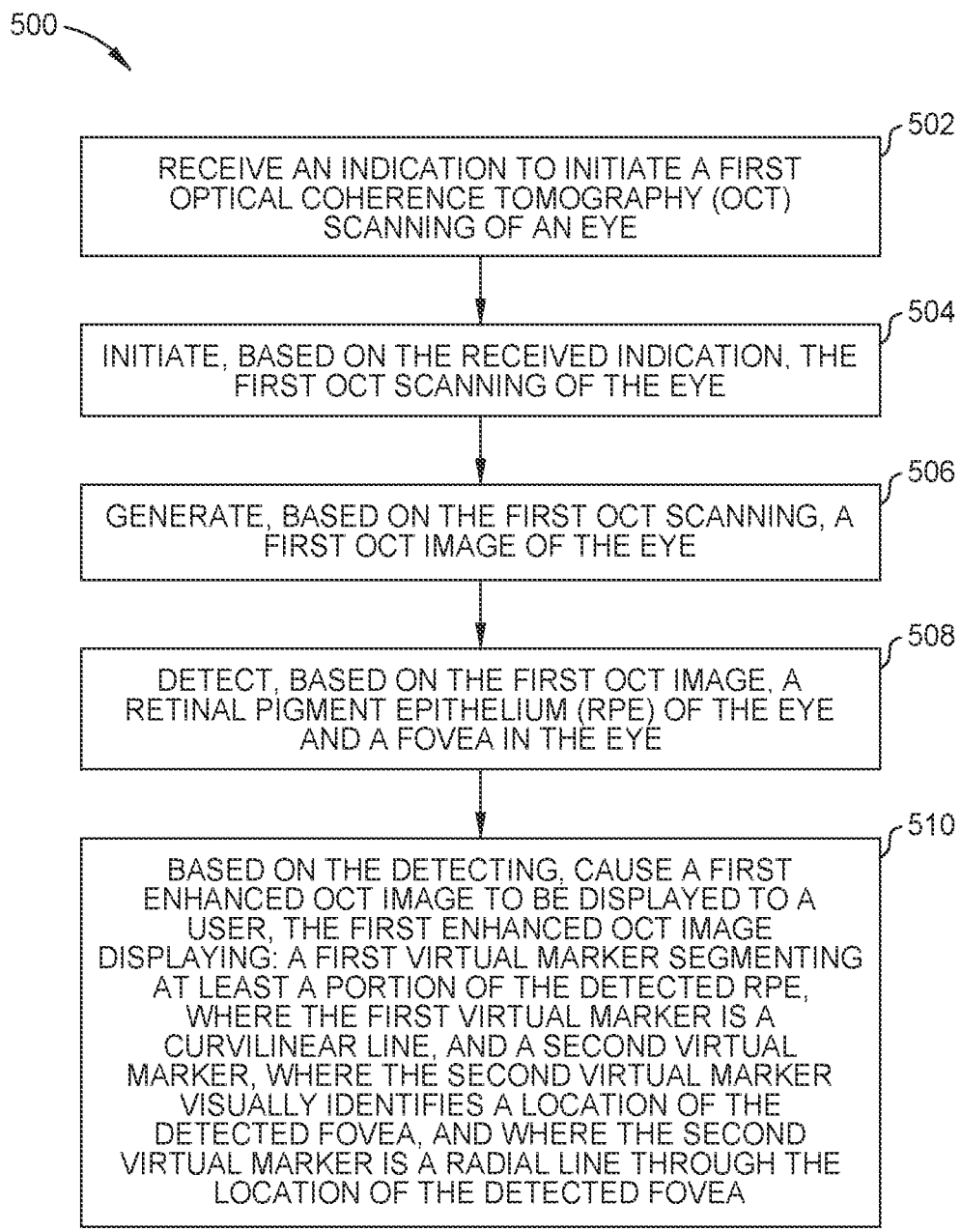
FIG. 5 illustrates a flow chart of an example method for displaying imaging markers on ophthalmic images, in accordance with an illustrative implementation of the present disclosure.

FIG. 5 illustrates a flow chart of an example method for displaying imaging markers on ophthalmic images, in accordance with an illustrative implementation of the present disclosure. The operations 500 may be performed, for example, by an OCT controller (e.g., the OCT controller 104 of imaging system 100). The operations 500 may be implemented as software components that are executed and run on one or more processors (e.g., processor 201).

The operations 500 may begin at 502, where the OCT controller 104 receives an indication to initiate a first optical OCT scanning of an eye. At 504, the OCT controller 104 initiates, based on the received indication, the first OCT scanning of the eye (e.g., a full eye scan, a retina scan, and the like). At 506, the OCT controller 104, generates based on the first OCT scanning (e.g., based on scan data), a first OCT image of the eye (e.g., OCT image 300a, OCT image 400a). At 508, the OCT controller 104, detects, based on the first OCT image, a retinal pigment epithelium (RPE) of the eye and a fovea in the eye. At 510, the OCT controller 104, based on the detecting, causes a first enhanced OCT image to be displayed to a user, where the first enhanced OCT image (e.g., enhanced OCT image 300b, enhanced OCT image 400b) displays: a first virtual marker (e.g., virtual marker 305, virtual marker 401) segmenting at least a portion of the detected RPE, where the first virtual marker is a curvilinear line, and a second virtual marker (e.g., virtual marker 306, virtual marker 402), where the second virtual marker visually identifies a location of the detected fovea, and where the second virtual marker is a radial line through the location of the detected fovea.

In some implementations, the OCT controller 104, detects, based on the first OCT image, an abnormal macular anatomic configuration (e.g., abnormal macular condition) in the eye, and in response to detecting the abnormal macular anatomic configuration, the OCT controller 104 transmits an alert to the user advising against using a multi-focal IOL (e.g., a contrast decreasing multi-focal or EDOF IOL).

In some implementations, the OCT controller 104, initiates, in response to the completion of the first OCT scanning, a second OCT scanning of the eye. In some implementations, the OCT controller 104 generates, based on the second OCT scanning, a second OCT image of the eye. In some implementations, the OCT controller 104 detects, based on the second OCT image, the RPE in the eye and the fovea in the eye. In some implementations, the OCT controller 104 displays, based on the detecting, on a second enhanced OCT image: a third virtual marker (e.g., virtual marker 305, virtual marker 401) segmenting at least a same portion of the detected RPE as the first virtual marker, a fourth virtual marker (e.g., virtual marker 306, virtual marker 402) across at least a same portion of the location of the detected fovea as the first virtual marker. In some implementations, the OCT controller 104 causes the second enhanced OCT image to be displayed (e.g., via display 106) to the user.

In some implementations, the OCT controller 104 transmits an alert to the user, where the alert requests the user to confirm whether the fovea is accurately detected at least in one of the first enhanced OCT image or the second OCT enhanced image. In some implementations, the second OCT scanning of the eye is a retinal scanning of the eye and the second OCT image of the eye is a retinal image of the eye (e.g., image 400a).

In some implementations, the third virtual marker (e.g., virtual marker 305, virtual marker 401) is a curvilinear line and wherein a curvature of the curvilinear line matches a posterior curvature of the eye. In some implementations, the first virtual marker (e.g., virtual marker 305, virtual marker 401) and the second virtual marker (e.g., virtual marker 306, virtual marker 402) intersect perpendicularly. In some implementations, the fourth virtual marker is a straight line (e.g., a radial line through the location of the detected fovea).

In some implementations, the second virtual marker (e.g., virtual marker 306) is extended through an anterior portion of a retina of the eye on the first enhanced OCT image (e.g., image 300b). In some implementations, the first OCT image (e.g., image 300a) is an OCT B-scan image and a full biometry of the eye.

The methods and apparatus described above provide novel systems and methods for displaying virtual imaging markers that may be utilized to improve accuracy and verification of biometric measurements of a patient's eye. For example, the described systems and methods improve a user's ability to efficiently and accurately verify whether axial length measurements are determined correctly by an imaging system.

While the foregoing is directed to embodiments of the present disclosure, other and further embodiments of the disclosure may be devised without departing from the basic scope thereof, and the scope thereof is determined by the claims that follow.

Embodiment 1: An imaging system, comprising: a memory comprising computer-executable instructions; a processor configured to execute the computer-executable instructions and cause the imaging system to: receive an indication to initiate a first optical coherence tomography (OCT) scanning of an eye; initiate, based on the received indication, the first OCT scanning of the eye; generate, based on the first OCT scanning, a first OCT image of the eye; detect, based on the first OCT image, a retinal pigment epithelium (RPE) of the eye and a fovea in the eye; based on the detecting, cause a first enhanced OCT image to be displayed to a user, the first enhanced OCT image displaying: a first virtual marker segmenting at least a portion of the detected RPE, where the first virtual marker is a curvilinear line, and a second virtual marker, wherein the second virtual marker visually identifies a location of the detected fovea, and wherein the second virtual marker is a radial line through the location of the detected fovea; initiate, in response to the completion of the first OCT scanning, a second OCT scanning of the eye; generate, based on the second OCT scanning, a second OCT image of the eye; detect, based on the second OCT image, the RPE of the eye and the fovea in the eye; display, based on the detecting, on a second enhanced OCT image: a third virtual marker segmenting at least a same portion of the detected RPE as the first virtual marker, and a fourth virtual marker across at least a same portion of the location of the detected fovea as the first virtual marker; and cause the second enhanced OCT image to be displayed to the user.

The imaging system of embodiment 1, wherein the second OCT scanning of the eye is a retinal scanning of the eye and wherein the second OCT image of the eye is a retinal image of the eye.

The imaging system of embodiment 1, wherein the third virtual marker is a curvilinear line and wherein a curvature of the curvilinear line matches a posterior curvature of the eye.

The imaging system of embodiment 1, wherein the first virtual marker and the second virtual marker intersect perpendicularly.

The imaging system of embodiment 1, wherein the second virtual marker is extended through an anterior portion of a retina of the eye on the first enhanced OCT image.

The imaging system of embodiment 1, wherein the first OCT image is an OCT B-scan image and a full biometry of the eye.

What is claimed is:
1. A method comprising:
receiving an indication to initiate a first optical coherence tomography (OCT) scanning of an eye;
initiating, based on the received indication, the first OCT scanning of the eye;
generating, based on the first OCT scanning, a first OCT image of the eye;
detecting, based on the first OCT image, a retinal pigment epithelium (RPE) of the eye and a fovea in the eye;
based on the detecting, causing a first enhanced OCT image to be displayed to a user, the first enhanced OCT image displaying:
a first virtual marker segmenting at least a portion of the detected RPE, wherein the first virtual marker is a curvilinear line, and
a second virtual marker, wherein the second virtual marker visually identifies a location of the detected fovea, and wherein the second virtual marker is a radial line through the location of the detected fovea;
detecting, based on the first OCT image, an abnormal macular anatomic configuration in the eye; and in response to detecting the abnormal macular anatomic configuration, transmitting an alert to the user advising against using a contrast decreasing multifocal intraocular optical lens (IOL).

2. The method of claim 1, further comprising:
initiating, in response to the completion of the first OCT scanning, a second OCT scanning of the eye;
generating, based on the second OCT scanning, a second OCT image of the eye;
detecting, based on the second OCT image, the RPE of the eye and the fovea in the eye;
displaying, based on the detecting, on a second enhanced OCT image:
   a third virtual marker segmenting at least a same portion of the detected RPE as the first virtual marker, and
   a fourth virtual marker across at least a same portion of the location of the detected fovea as the first virtual marker;
causing the second enhanced OCT image to be displayed to the user.

3. The method of claim 2, further comprising:
transmitting an alert to the user, wherein the alert requests the user to confirm whether the fovea is accurately detected at least in one of the first enhanced OCT image or the second OCT enhanced image.

4. The method of claim 2, wherein the second OCT scanning of the eye is a retinal scanning of the eye and wherein the second OCT image of the eye is a retinal image of the eye.

5. The method of claim 2, wherein the third virtual marker is a curvilinear line and wherein a curvature of the curvilinear line matches a posterior curvature of the eye.

6. The method of claim 1, wherein the first virtual marker and the second virtual marker intersect perpendicularly.

7. The method of claim 1, wherein the second virtual marker is extended through an anterior portion of a retina of the eye on the first enhanced OCT image.

8. The method of claim 1, wherein the first OCT image is an OCT B-scan image and a full biometry of the eye.

9. An imaging system, comprising:
a memory comprising computer-executable instructions;
a processor configured to execute the computer-executable instructions and cause the imaging system to:
   receive an indication to initiate a first optical coherence tomography (OCT) scanning of an eye;
   initiate, based on the received indication, the first OCT scanning of the eye;
   generate, based on the first OCT scanning, a first OCT image of the eye;
   detect, based on the first OCT image, a retinal pigment epithelium (RPE) of the eye and a fovea in the eye;
   based on the detecting, cause a first enhanced OCT image to be displayed to a user, the first enhanced OCT image displaying:
      a first virtual marker segmenting at least a portion of the detected RPE, wherein the first virtual marker is a curvilinear line, and
      a second virtual marker, wherein the second virtual marker visually identifies a location of the detected fovea, and wherein the second virtual marker is a radial line;
   detect, based on the first OCT image, an abnormal macular anatomic configuration in the eye; and
   in response to detecting the abnormal macular anatomic configuration, transmit an alert to the user advising against using a contrast decreasing multifocal intraocular optical lens (IOL).

10. The imaging system of claim 9, wherein the processor is further configured to cause the imaging system to:
initiate, in response to the completion of the first OCT scanning, a second OCT scanning of the eye;
generate, based on the second OCT scanning, a second OCT image of the eye;
detect, based on the second OCT image, the RPE of the eye and the fovea in the eye;
display, based on the detecting, on a second enhanced OCT image:
   a third virtual marker segmenting at least a same portion of the detected RPE as the first virtual marker, and
   a fourth virtual marker across at least a same portion of the location of the detected fovea as the first virtual marker; and
cause the second enhanced OCT image to be displayed to the user.

11. The imaging system of claim 10, wherein the processor is further configured to cause the imaging system to:
transmit an alert to the user, wherein the alert requests the user to confirm whether the fovea is accurately detected at least in one of the first enhanced OCT image or the second OCT enhanced image.

12. The imaging system of claim 10, wherein the second OCT scanning of the eye is a retinal scanning of the eye and wherein the second OCT image of the eye is a retinal image of the eye.

13. The imaging system of claim 10, wherein the third virtual marker is a curvilinear line and wherein a curvature of the curvilinear line matches a posterior curvature of the eye.

* * * * *